(12) United States Patent
Schauderna

(10) Patent No.: US 10,525,193 B2
(45) Date of Patent: Jan. 7, 2020

(54) LARGE VOLUME SKIN PATCH MEDICAMENT DELIVERY DEVICE WITH INTEGRATED SKIN STERILIZATION MECHANISM FOR THE INJECTION SITE

(71) Applicant: Sanofi, Paris (FR)

(72) Inventor: Florian Schauderna, Frankfurt am Main (DE)

(73) Assignee: Sanofi, Paris (FR)

( * ) Notice: Subject to any disclaimer, the term of this patent is extended or adjusted under 35 U.S.C. 154(b) by 170 days.

(21) Appl. No.: 15/508,834

(22) PCT Filed: Sep. 11, 2015

(86) PCT No.: PCT/EP2015/070869
§ 371 (c)(1),
(2) Date: Mar. 3, 2017

(87) PCT Pub. No.: WO2016/041871
PCT Pub. Date: Mar. 24, 2016

(65) Prior Publication Data
US 2017/0290977 A1    Oct. 12, 2017

(30) Foreign Application Priority Data

Sep. 15, 2014    (EP) .................................... 14306419

(51) Int. Cl.
*A61M 5/142*    (2006.01)
*A61M 5/20*    (2006.01)
(Continued)

(52) U.S. Cl.
CPC ....... *A61M 5/14248* (2013.01); *A61L 2/0082* (2013.01); *A61L 2/26* (2013.01);
(Continued)

(58) Field of Classification Search
CPC ...... A61L 2202/15; A61L 2/0082; A61L 2/26; A61M 11/00; A61M 2005/14252;
(Continued)

(56) References Cited

U.S. PATENT DOCUMENTS 4,031,889 A    6/1977 Pike
2006/0264926 A1    11/2006 Kochamba et al.
(Continued)

FOREIGN PATENT DOCUMENTS

GB    770 341    3/1957
JP    2007-520269    7/2007
(Continued)

OTHER PUBLICATIONS

Information Disclosure Statement and Written Opinion in International Application No. PCT/EP2015/070869, dated Nov. 25, 2015, 12 pages.
(Continued)

*Primary Examiner* — Imani N Hayman
(74) *Attorney, Agent, or Firm* — Fish & Richardson P.C.

(57) ABSTRACT

A medicament delivery device comprises a housing containing a medicament delivery mechanism including an injection needle. A sterilizing mechanism is connected to the housing. An adhesive surface provides for securing the housing to a patient's skin during a medicament delivery process. The sterilizing mechanism is configured such that, in use once the housing is secured to a patient's skin, the sterilizing mechanism can be operated to sterilize an area of the patient's skin to serve as an injection site.

15 Claims, 8 Drawing Sheets

(51) Int. Cl.
*A61L 2/00* (2006.01)
*A61L 2/26* (2006.01)
*A61M 5/145* (2006.01)
*A61M 5/158* (2006.01)
*A61M 5/172* (2006.01)
*A61M 5/42* (2006.01)
*A61M 11/00* (2006.01)
*A61M 5/315* (2006.01)

(52) U.S. Cl.
CPC .......... *A61M 5/1452* (2013.01); *A61M 5/158* (2013.01); *A61M 5/172* (2013.01); *A61M 5/20* (2013.01); *A61M 5/422* (2013.01); *A61M 11/00* (2013.01); *A61L 2202/15* (2013.01); *A61M 2005/14252* (2013.01); *A61M 2005/206* (2013.01); *A61M 2005/208* (2013.01); *A61M 2005/2073* (2013.01); *A61M 2005/31588* (2013.01); *A61M 2205/0205* (2013.01); *A61M 2205/13* (2013.01); *A61M 2205/586* (2013.01)

(58) Field of Classification Search
CPC .... A61M 2005/206; A61M 2005/2073; A61M 2005/208; A61M 2005/3158; A61M 2205/0205; A61M 2205/13; A61M 2205/586; A61M 5/14248; A61M 5/1452; A61M 5/158; A61M 5/422; A61M 5/172; A61M 5/20

See application file for complete search history.

(56) References Cited

U.S. PATENT DOCUMENTS

2011/0105951 A1 5/2011 Bernstein et al.
2012/0010594 A1 1/2012 Holt et al.
2012/0022448 A1 1/2012 Stumber

FOREIGN PATENT DOCUMENTS

| JP | 2012-521817 | 9/2012 |
| JP | 2013-528107 | 7/2013 |
| WO | WO 2005/065551 | 7/2005 |
| WO | WO 2011/156373 | 12/2011 |

OTHER PUBLICATIONS

International Preliminary Report on Patentability in International Application No. PCT/EP2015/070869, dated Mar. 21, 2017, 8 pages.

LARGE VOLUME SKIN PATCH MEDICAMENT DELIVERY DEVICE WITH INTEGRATED SKIN STERILIZATION MECHANISM FOR THE INJECTION SITE

CROSS-REFERENCE TO RELATED APPLICATIONS

This application is a U.S. national stage application under 35 USC § 371 of International Application No. PCT/EP2015/070869, filed on Sep. 11, 2015, which claims priority to European Patent Application No. 14306419.4, filed on Sep. 15, 2014, the entire contents of which are incorporated herein by reference.

FIELD

The present disclosure relates to a device for delivery of medicament to a patient.

BACKGROUND

A variety of diseases exist that require regular treatment by injection of a medicament and such injections can be performed by using injection devices. Various injection devices for delivering injections of medicament are known in the art. Another type of injection pump that is gaining traction is the bolus injector device. Some bolus injector devices are intended to be used with relatively large volumes of medicament, typically at least 1 ml and maybe a few ml. Injection of such large volumes of medicament can take some minutes or even hours. Such high capacity bolus injector devices can be called large volume devices (LVDs). Generally, such devices are operated by the patients themselves, although they may also be operated by medical personnel.

To use an injector device, such as an LVD, it is first supported on a suitable injection site on a patient's skin. Once installed, injection is initiated by the patient or another person (user). Typically, the initiation is effected by the user operating an electrical switch, which causes a controller to operate the device. Operation includes firstly injecting a needle into the user and then causing the injection of medicament into the user's tissue. Biological medicaments are being increasingly developed which comprise higher viscosity injectable liquids and which are to be administered in larger volumes than long-known liquid medicaments. LVDs for administering such biological medicaments may comprise a pre-filled disposable drug delivery device or, alternatively, a disposable drug delivery device into which a patient or medical personnel must insert a drug cartridge prior to use.

Particularly in the case of patient-operated LVDs which require insertion of a drug cartridge prior to use, the drug delivery process from start to finish can be a complicated multi-step process, including gathering of all of the device components, assembly of the components to produce the LVD ready for drug administration and sterilization of the injection site before the actual process of injecting the drug can even begin. For example, the preparation step includes sourcing a sterilizing liquid and a sterilizing swab to apply the sterilizing liquid. The sterilizing liquid then needs to be applied over the intended injection site on a patient's body to ensure the injection site is fully sterilized, and the sterilizing materials then put aside or discarded before a medicament administration procedure can be commenced. Gathering all these materials and performing the sterilizing process is time-consuming and burdensome, and adds complication to the process for the patient. This renders the process intrusive upon his or her daily schedule, and increases the risk that the patient may not correctly perform the drug administration.

There are limitations as to the maximum volume of liquid medicament one injection site can accept within a predetermined amount of time without causing the patient discomfort, pain, inhibiting pharmacokinetics or causing leakage out of the injection site. To avoid complications of such interactions between the drug and the patient's body, such large-volume biological medicaments should not be administered at the same injection site on the patient's body twice or more in succession. Therefore, this is another factor in the medicament administration process which the patient must take into consideration.

SUMMARY

Certain embodiments provide a medicament delivery device comprising a housing containing a medicament delivery mechanism including an injection needle, a sterilizing mechanism connected to the housing, an adhesive surface for securing the device to a patient's skin during a medicament delivery process, wherein the sterilizing mechanism comprises a sterilizing pad impregnated with a sterilizing agent, characterized in that the sterilizing pad is repeatedly moveable relative to the adhesive surface such that, in use when the device is secured to a patient's skin, the sterilizing pad can be repeatedly moved in contact with the patient's skin to sterilize an area of the patient's skin to serve as an injection site. This may advantageously reduce the amount of separate materials a user must gather for a medicament delivery procedure. This may advantageously ensure thorough and effective sterilizing of the skin. This may also make the device simpler to use.

The sterilizing pad may be movable to sweep or wipe across a patient's skin. The sterilizing pad may be movable in a plane substantially parallel to the adhesive surface. The sterilizing pad may be moveable towards and away from the skin. The sterilizing pad may be movable in a plane substantially perpendicular to the adhesive surface. This may advantageously provide an efficient and effective sterilization of the patient's skin.

The sterilizing pad may be mounted on a carrier. This may advantageously enable separate manufacture of a carrier and sterilizing pad to the rest of the device, which may be cost effective and/or simpler for manufacture.

The sterilizing pad may be received within a recess in the carrier. This may advantageously give lateral support to the sterilizing pad when being wiped. This may advantageously allow a thicker or more absorbent pad to be provided, to carry more sterilizing agent. This may advantageously provide space for the pad to be compressed into while being stored before use.

The carrier may be moveably mounted to the housing. This may advantageously allow movement of the sterilizing pad across the skin without requiring movement of the housing.

The carrier may comprise a rotatable plate. This may advantageously provide a compact and space-efficient device configuration. Alternatively, the carrier may comprise a slidable plate. This may advantageously enable an alternative configuration of device to be produced.

The injection needle may be moveable between a retracted position in which it is fully disposed within the housing and an engaged position in which it projects from the housing to inject a patient's skin in use, and the carrier may be moveable between a first position and a second position, the injection needle may be prevented from moving into the engaged position when the carrier is in the first position. This may advantageously provide a safety feature of preventing patient injection before an injection site on the patient's skin has been sterilized.

When the carrier is in the first position, the carrier may block the path of the injection needle to prevent it being moveable into the engaged position, and when the carrier is in the second position, the injection needle may be free to move into the engaged position. This may advantageously provide a safety feature by the carrier physically blocking the needle when the carrier is in the first position.

The carrier may comprise a circular plate with a sector absent and, in the second position of the carrier, the absent sector of the plate may be aligned with the injection needle such that the injection needle can pass through the absent sector and into the engaged position. This may advantageously enable a safety feature in a compact device configuration.

The medicament delivery mechanism may be coupled to the carrier such that the medicament delivery mechanism is prevented from operating when the carrier is in the first position and is operable when the carrier is in the second position. This may advantageously provide an alternative safety feature to prevent injection on an injection site before sterilization.

The medicament delivery mechanism may be actuated by a button on the housing and the button may be prevented from actuating the medicament delivery mechanism when the carrier is in the first position. This may advantageously provide a further safety feature to mitigate the risk of accidental operation of the device.

The medicament delivery mechanism may be electronically controlled and electrical power to actuate the medicament delivery mechanism may be prevented when the carrier is in the first position. This may advantageously provide an embodiment of a feature to avoid accidental device activation.

The carrier may be coupled to a control knob mounted on an outer surface of the housing and the carrier may be manually moved by moving the control knob. This may advantageously provide a simple device construction, allowing economy of manufacture. It may also allow a patient or other user an added degree of control over the skin sterilization process.

The sterilizing agent may comprise a dye to stain a patient's skin. This may advantageously identify last injection site and allow a user or patient to avoid using same injection site consecutively.

The sterilizing agent may comprise a gel. This may advantageously be less liable to leak from the device, and less susceptible to evaporation, and may thereby enable a longer storage or shelf life of device.

The sterilizing mechanism may comprise a spray nozzle connected to a source of sterilizing agent. The source of sterilizing agent may comprise a pressurized container of sterilizing agent. This may advantageously provide an alternative configuration of sterilizing mechanism to a moveable sterilizing pad.

The housing may be moveably mounted to a base plate, and the sterilizing pad may be secured to the housing to extend into contact with a patient's skin when the device is secured to a patient. The sterilizing pad may extend though an aperture in the base plate. The sterilizing pad may move across a patient's skin when the housing is moved relative to the base plate. The housing may be rotatable relative to the base plate. This may advantageously allow an alternative configuration of medicament delivery device with integrated sterilizing mechanism. Operation of the device may be linked to movement of the housing relative to the base plate.

The medicament delivery device may be fitted with a container of medicament.

The medicament delivery device may include a mechanism that prevents operation of the sterilizing mechanism before the device is secured to a patient. Such mechanism may include a switch or detector on device which is linked to the sterilizing mechanism and which is actuated when the device is secured to the patient. Such detector may comprise an electrical sensor or a mechanically depressed button on the adhesive surface of the device. This may advantageously prevent accidental activation of the sterilizing mechanism before the device is secured to a patient.

The sterilizing agent with which the sterilizing pad is impregnated, or which is provided from the sterilizing mechanism, for example from a spray nozzle, may include a topical anesthetic. This may advantageously locally anesthetize an area of the patient's skin that is sterilized. This may advantageously reduce pain or discomfort that may otherwise be caused by injection of the needle into the patient's skin.

Additional aspects provide a method of use of a medicament delivery device comprising a housing containing a medicament delivery mechanism including an injection needle, a sterilizing mechanism connected to the housing, and an adhesive surface for securing the housing to a patient's skin during a medicament delivery process, the method comprising securing housing to a patient's skin, actuating the sterilizing mechanism to sterilize an area of the patient's skin to serve as an injection site, and commencing a medicament administration process Medicament delivery devices described herein can advantageously be simple to use and can thus help to reduce the risk of incorrect use by a user.

BRIEF DESCRIPTION OF THE DRAWINGS

Embodiments will now be described, by way of example only, with reference to the accompanying drawings, in which.

DETAILED DESCRIPTION

Figure 1:
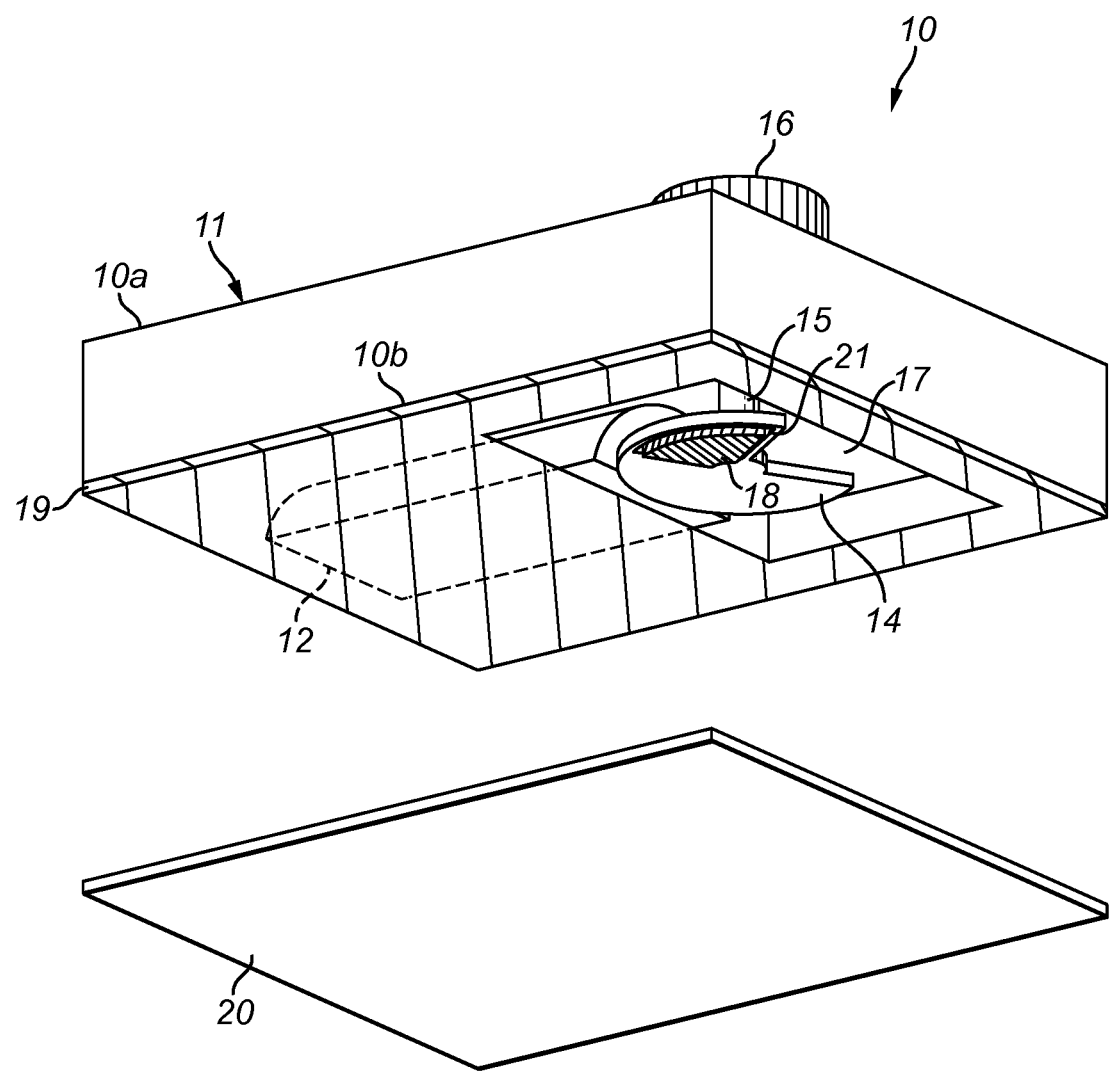
FIG. 1 shows a perspective view of a medicament delivery device of a first embodiment.

FIGS. 1 to 4 show a medicament delivery device 10, which in the exemplary embodiment comprises a bolus injector device (hereafter simply referred to as "device 10"), according to a first embodiment which comprises a housing 11 containing a medicament delivery mechanism 12. The device 10 can include an LVD. The medicament delivery mechanism is only shown schematically and a number of the functional components are omitted for the sake of clarity and brevity, but the medicament delivery mechanism 12 includes a needle 13 for injection of the liquid medicament into a patient's body. The liquid medicament may be provided in a reservoir (not shown) within the medicament delivery mechanism 12, or may be provided externally of the device 10. The housing 11 also contains a moveable plate 14 configured to move relative to the housing 11. In the embodiment shown in FIGS. 1 to 4, the plate 14 is rotatably connected via a shaft 15 to an actuator, which in the first embodiment comprises a knob 16, on the outside of the housing 11. However, other configurations of plate 14 and actuator are intended within the scope of the invention, as discussed below.

A medicament delivery mechanism 12 of a device may include one or more of the following components. A controller configured to control operation of the device 10. A needle insertion mechanism to insert the needle 13 into a patient from a retracted position into an engaged position. A needle driver to drive the needle insertion mechanism, for example an electric motor or a spring mechanism. An energy source to power the needle driver. A medicament reservoir containing a supply of medicament to be administered to a patient. The medicament reservoir may, for example, include a cartridge or a vial formed of glass. A plunger maybe provided within the cartridge and plunger driver mechanically coupled to the plunger. The plunger driver may be controllable to move the plunger along the medicament cartridge. The force provided by the plunger causes medicament to be expelled through a medicament delivery aperture in the medicament cartridge and along a medicament delivery tube to the needle 13 to be expelled through the bore of the needle 13. An electrical power source in the form of a battery to power to the controller. The battery may also provide electrical power the plunger driver, if this is an electrically driven device. The battery may also constitute the energy source for the needle driver.

Figure 5:
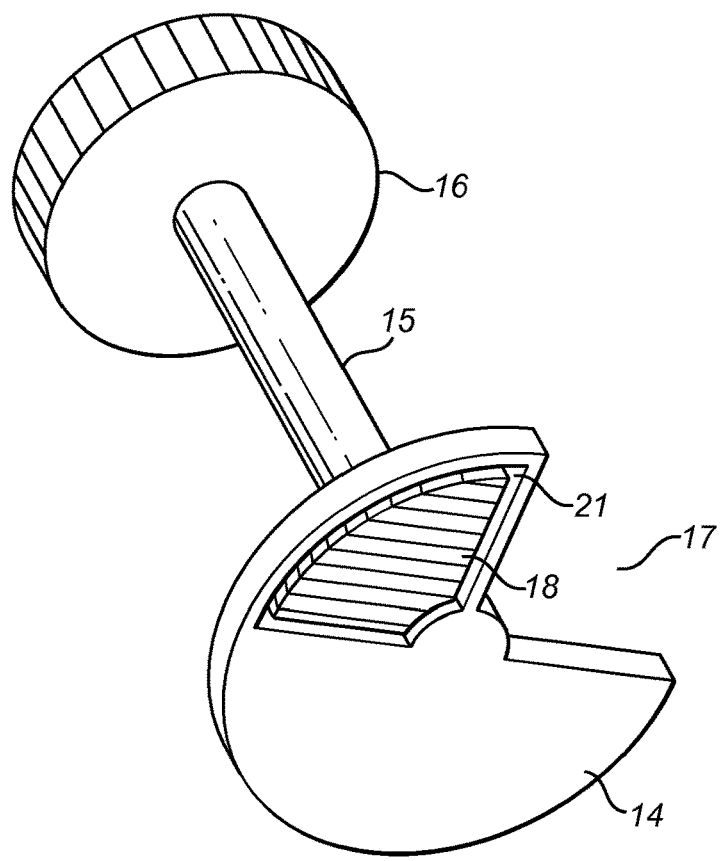
FIG. 5 shows a perspective view from below of a rotatable component of the medicament delivery device of FIGS. 1 to 4.
Figure 6:
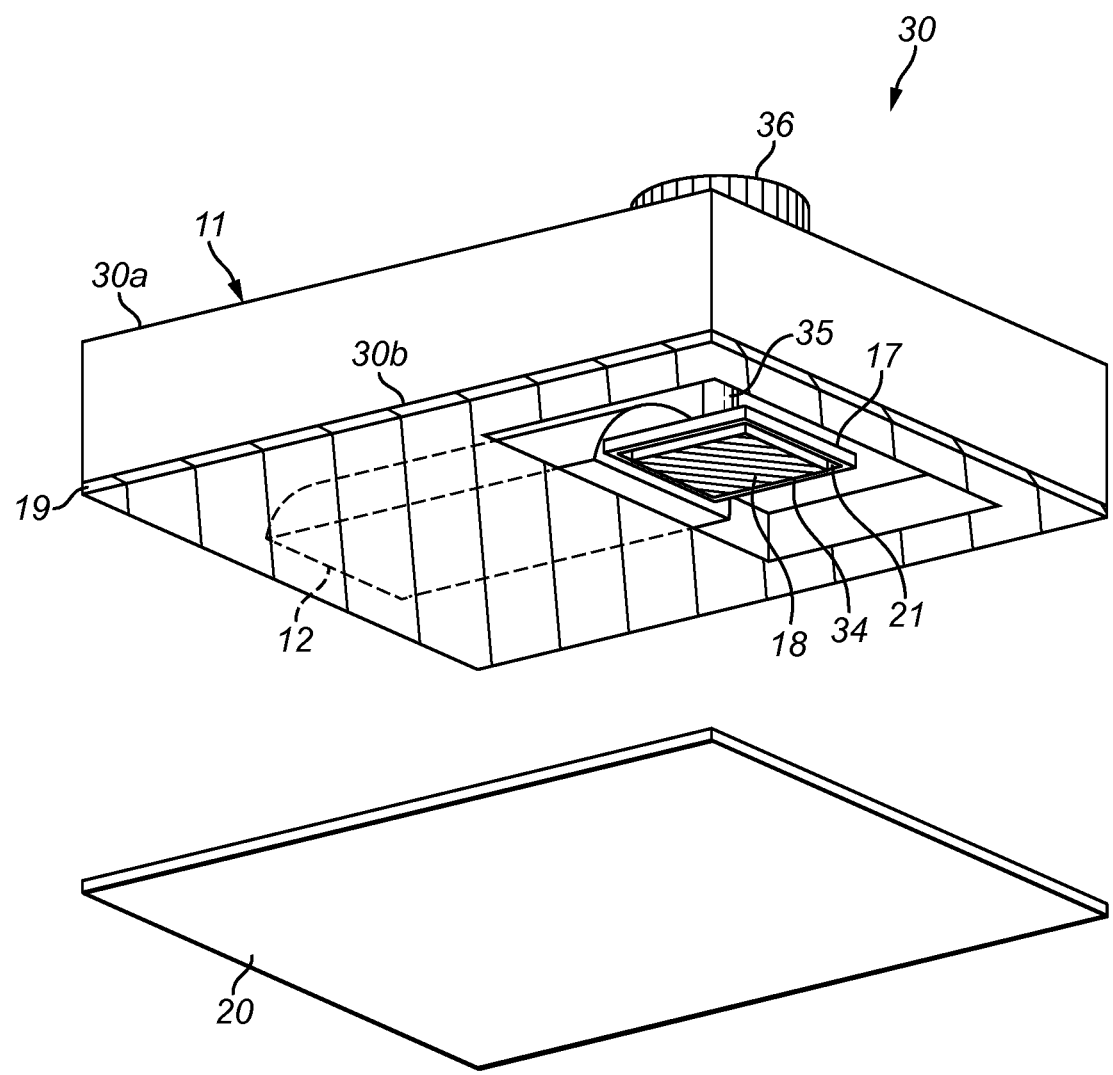
FIG. 6 shows a perspective view of a medicament delivery device of a second embodiment.

FIG. 5 shows the plate 14, shaft 15 and knob 16 in more detail, and it can be seen that the rotatable plate 14 is circular but is formed as an incomplete disc and includes an open sector 17 around a portion of the circumference of the plate 14. In the exemplary embodiment shown in FIGS. 1 to 5, the open sector 17 extends over approximately a 90 degree sector of the circumference of the rotatable plate 14.

A surface of the rotatable plate 14 remote from the knob 16 includes a sterilizing pad 18 impregnated with a sterilizing agent, such as alcohol. The sterilizing pad 18 may be made of any suitable material such as sponge, cotton wool or cotton gauze, for example. The sterilizing pad 18 is shaped as a sector of the circular rotatable plate 14.

Figure 2:
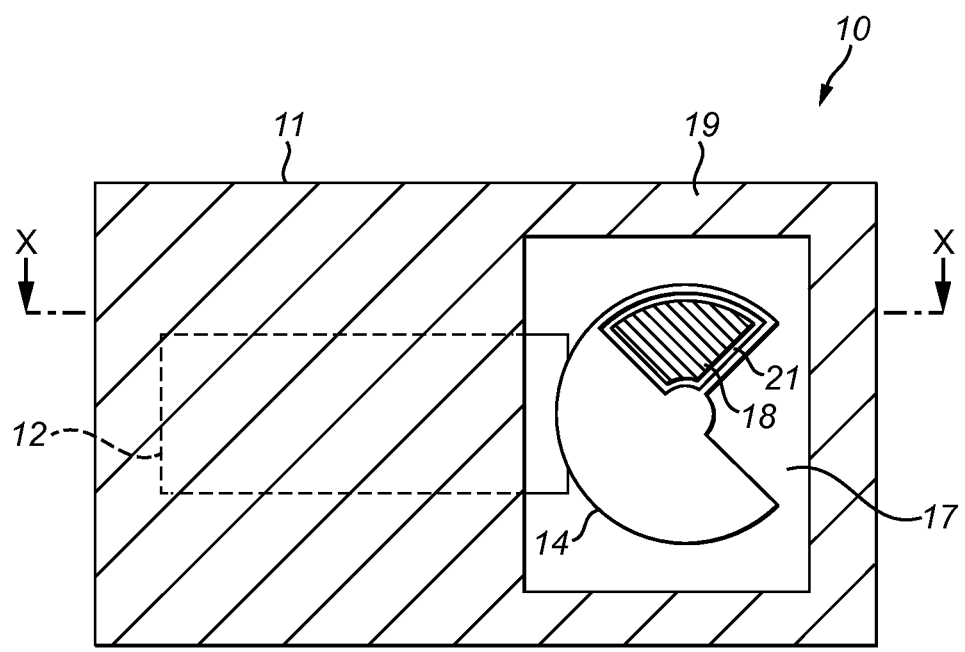
FIG. 2 shows a plan view from below of the medicament delivery device of FIG. 1 in a first position.
Figure 3:
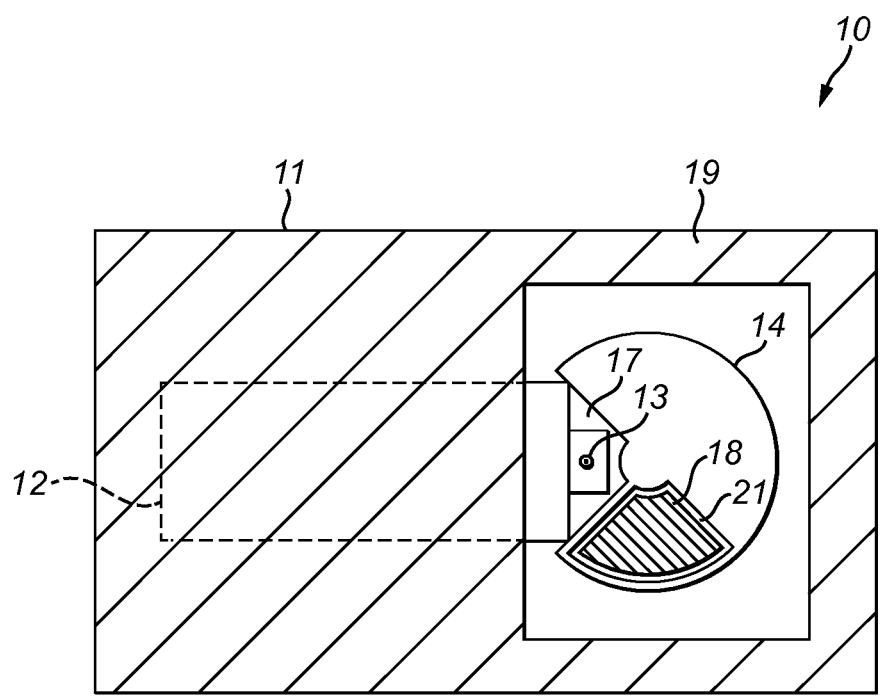
FIG. 3 shows a plan view from below of the medicament delivery device of FIG. 1 in a second position.
Figure 4:
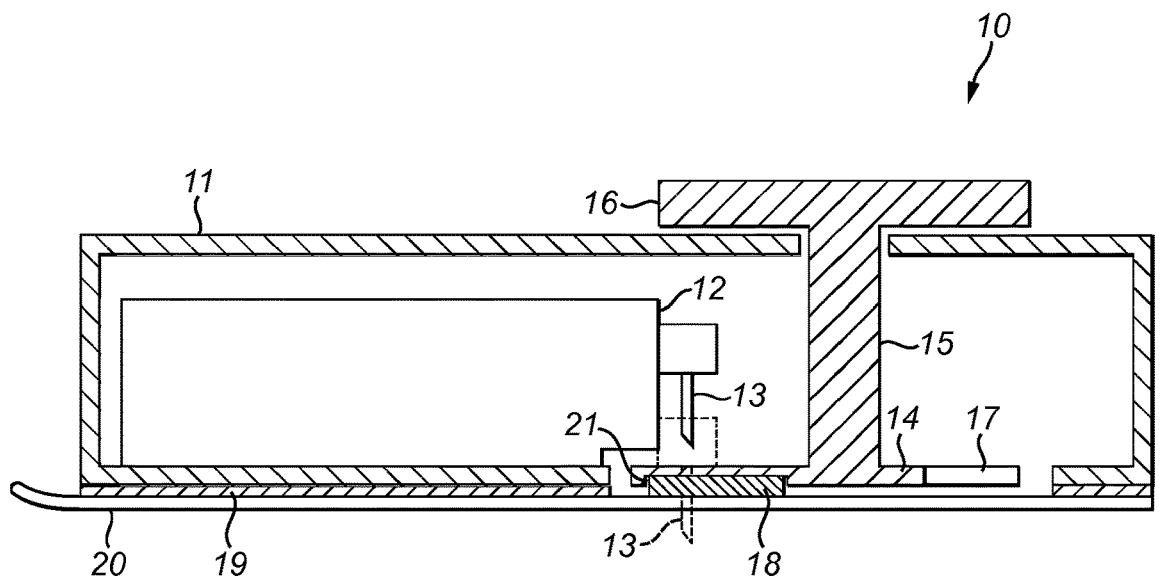
FIG. 4 shows a cross-section of the medicament delivery device along the line X-X shown in FIG. 2.

It can be seen from FIGS. 2 and 3 that the rotatable plate 14 is moveable between a first position (FIG. 2) to a second position (FIG. 3), and is manually moveable by a user turning the knob 16. The first position corresponds to a pre-use position of the device 10—namely the configuration of the device 10 as provided to a patient before use. The second position corresponds to an operative position of the device 10—namely a configuration of the device 10 once a patient has turned the knob 16 to move the rotatable plate 14 from the first position and the device 10 is primed ready to commence an injection/medicament administration step.

The device 10 generally comprises an upper side 10a on which the knob 16 is disposed, and a lower side 10b upon which the sterilizing pad 18 is disposed such that the rotatable plate 14 is substantially flush with the lower side 10b. The lower side 10b of the device 10 includes an adhesive patch 19 for adhering the device 10 to a patient's skin during use. The lower side 10b of the device 10 also includes a removable cover sheet 20 which covers the adhesive patch 19 and the sterilizing pad 18 prior to use and is removed by a patient before using the device 10.

The needle 13 of the medicament delivery mechanism 12 is moveable between a retracted position and an engaged position. In the retracted position (shown in solid lines in FIG. 4) the needle 13 is disposed within the housing 11 of the device 10, and in the engaged position (shown in dashed lines in FIG. 4) the needle 13 projects from the lower side 10b of the device 10 so as to pierce and inject a patient's skin when the device 10 is attached to a patient. In the retracted position, the needle 13 is positioned between the rotatable plate 14 and the upper side of the device 10a. Also, in the retracted position of the needle 13 and the first position of the rotatable plate 14, the rotatable plate 14 is positioned between the needle 13 and the lower side 10b of the device 10, thereby blocking the needle 13 from being moved into the engaged position.

Figure 13:
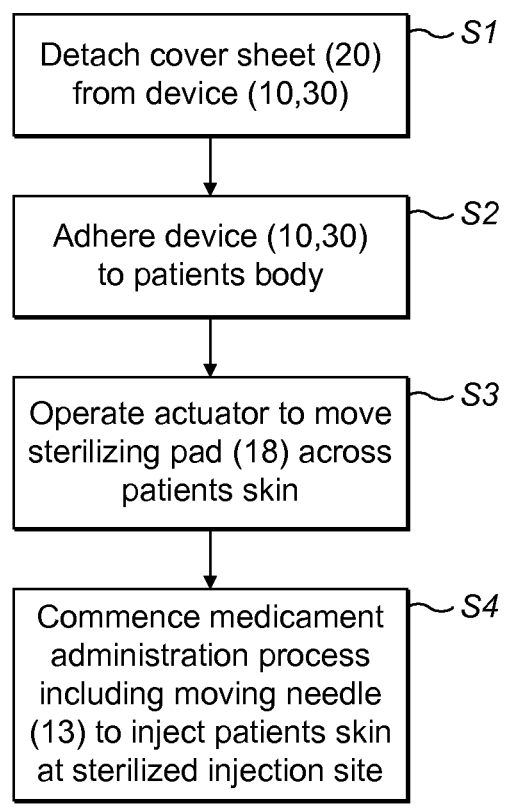
FIG. 13 shows a flow chart of steps of use of the medicament delivery device of the first or second embodiment shown in FIGS. 1 to 4 and 6 to 9.

Use of the device 10 will be described in the context of a self-administration process by a patient, with reference to the flow chart of FIG. 13. However, it will be appreciated that use of the device 10 is not limited to use by a patient and may be used by third parties for application to a patient, for example by medical personnel. In use of the device 10, at step S1, a patient detaches the cover sheet 20 from the lower side 10b of the device 10 to expose the adhesive patch 19 and the sterilizing pad 18. At step S2, the patient then adheres the device 10 to an appropriate part of their body to serve as an injection site of the relevant medicament. The adhesive patch 19 secures the device 10 to the patient during the subsequent medicament administration process.

Once adhered to the body, at step S3, the patient then rotates the knob 16 through 180 degrees to move the sterilizing pad 18 from the first position to the second position and in doing so, the sterilizing pad 18 sweeps across the area of the patient's skin directly beneath the needle 13—namely the intended injection site. This sweeping movement of the sterilizing pad 18 over the skin allows the alcohol or other sterilizing agent in the pad 18 to disinfect the injection site ready for the medicament delivery injection to take place. The movement of the rotatable plate 14 to the second (operative) position also aligns the open sector 17 of the rotatable plate 14 with the needle 13 so that the needle 13 is no longer blocked from the patient's skin by the rotatable plate 14 and is then able to move from the retracted position to the engaged position.

In a subsequent medicament delivery step, the medicament delivery mechanism 12 is actuated at step S4 to move the needle into the engaged position to pierce the patient's skin, and the medicament is then administered to the patient via the needle 13. The actuation of the medicament delivery mechanism 12 may be manually initiated by the user, for example by pressing a button (not shown), or may occur automatically once the rotatable plate 14 is moved into the second position.

It will be appreciated that the device 10 having a skin sterilizing mechanism incorporated into the device 10 eliminates the need for a user to perform a separate skin sterilizing step in the medicament administration process prior to securing the device 10 to their skin, thereby making the procedure simpler and quicker, and less burdensome for the patient. This also reduces the number of pieces of equipment and materials the user needs to assemble in preparation for their medicament administration process.

In addition to the above advantages, the configuration of device 10 of the first embodiment provides a safety feature of the rotatable plate 14 preventing the needle 13 from moving into the engaged position before the skin has been sterilized. The device 10 may include a further mechanism to prevent accidental actuation of the medicament delivery mechanism 12 before the rotatable plate 14 has been moved into the second position. For example, a projecting element (not shown) on the shaft 15 may lock an actuator button (not shown) until the shaft 15 is rotated sufficiently for the rotatable plate 14 to be in the second position. Alternatively, the medicament delivery mechanism 12 may be actuated automatically only when the rotatable plate 14 reaches the second position. For example, the medicament delivery mechanism 12 may be electronically powered by a battery and one or more actuation motors (not shown), and a connection between the battery and motors may not be made until the rotatable plate 14 reaches the second position. Alternatively, a controller (not shown) that enables actuation of the medicament delivery mechanism 12 may be mechanically or electronically linked to the position of the rotatable plate 14, shaft 15 or knob 16 so that the controller only actuates the medicament delivery mechanism 12 when the rotatable plate 14 reaches the second position.

The sterilizing pad 18 may be received within a recess 21 formed in the rotatable plate 14 so as to be at least partially embedded within the plate 14. This would provide the additional advantage of giving lateral support to the sterilizing pad 18 to counter the frictional resistance with the patient's skin as it sweeps across the patient's skin. The sterilizing pad 18 is preferably made from a compressible material and may initially be provided on the rotatable plate 14 in a compressed state and which, upon detachment of the removable label 20, expands to stand proud of the surface of the rotational plate 14 and/or of the lower side 10b of the device 10. This ensures that the sterilizing pad 18 makes good contact with the patient's skin in use. In a further optional embodiment, the sterilizing pad 18 may be initially compressed within a recess 21 in the rotatable plate 14 and retained in place by the cover sheet 20 being adhered to the surface of the rotatable plate 14 around the recess 21 within which the sterilizing pad 18 is received. Then, upon detachment of the cover sheet 20, the sterilizing pad 18 may expand to project beyond the surface of the rotatable plate 14.

The device 10 of the first embodiment shown in FIGS. 1 to 5 is configured such that the sterilizing pad 18 is mounted on a carrier (i.e. the rotational plate 14) so as to sweep across the patient's skin in an arcing, rotational movement. However, the invention is not intended to be limited to this configuration or motion, or this particular type of sterilizing pad carrier. Accordingly, a medicament delivery device 30 of a second embodiment is shown in FIGS. 6 to 9 and is similar to the device 10 of the first embodiment shown in FIGS. 1 to 5, and like features retain the same reference numerals and description thereof will not be repeated. The device 30 generally comprises an upper side 30a and a lower side 30b.

A difference between the device 30 of the second embodiment and the device 10 of the first embodiment is that the device 30 of the second embodiment does not include the rotatable plate 14 upon which the sterilizing pad 18 is mounted. Instead, the device 30 comprises a different configuration of sterilizing pad carrier, namely a siding plate 34 disposed within the housing 11, and the sterilizing pad 18 is provided on the sliding plate 34. The sliding plate 34 is connected to a knob 36 on the upper side 30a of the device 30 by a rigid web 35. A slot 37 is provided in the housing 11 in the upper side 30a of the device 30 and the web 35 extends through the slot 37. The sliding plate 34 can be slid across the device 30 in a translational movement by moving the knob 36 from one side of the device 30 to the other.

Figure 7:
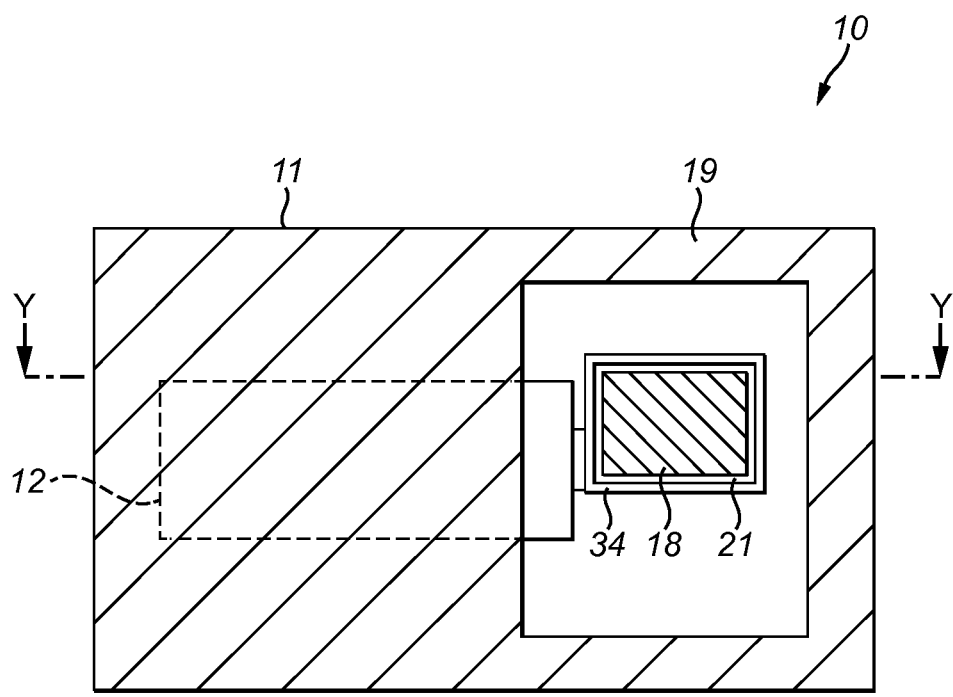
FIG. 7 shows a plan view from below of the medicament delivery device of FIG. 6 in a first position.
Figure 8:
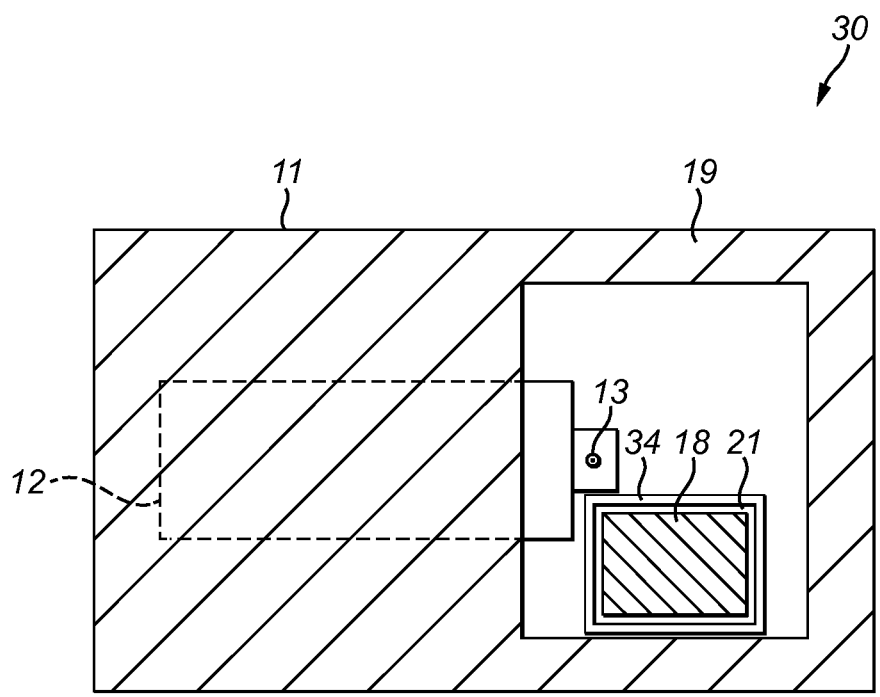
FIG. 8 shows a plan view from below of the medicament delivery device of FIG. 6 in a second position.
Figure 9:
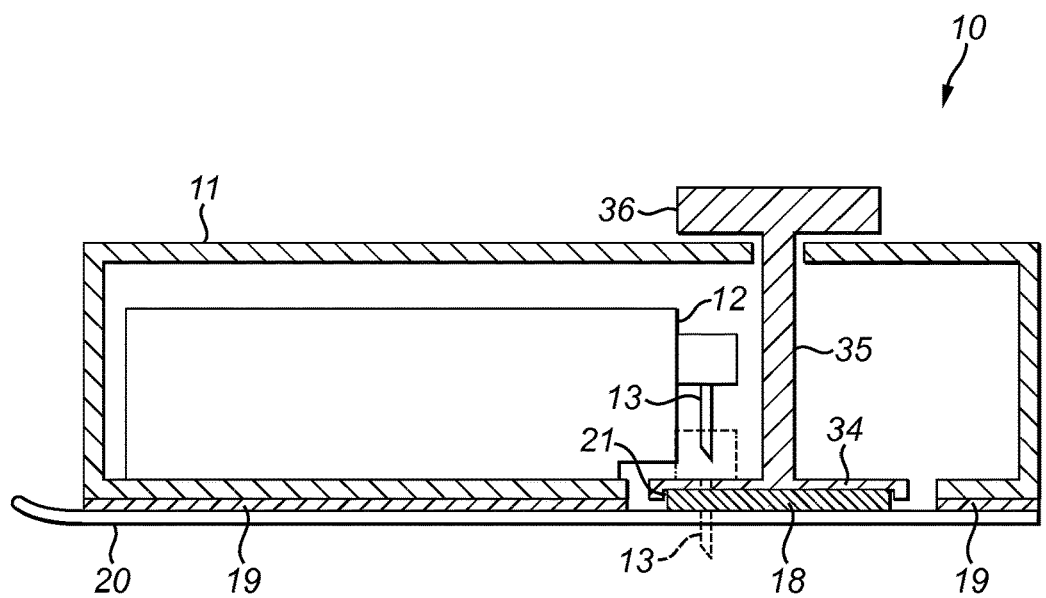
FIG. 9 shows a cross-section of the medicament delivery device along the line Y-Y shown in FIG. 7.

It can be seen from FIGS. 7 and 8 that the sliding plate 34 is moveable between a first position (FIG. 7) to a second position (FIG. 8), and is manually moveable by a user sliding the knob 36. The first position corresponds to a pre-use position of the device 30—namely the configuration of the device 10 as provided to a patient before use. The second position corresponds to an operative position of the device 30—namely a configuration of the device 30 once a patient has slid the knob 36 to move the sliding plate 34 from the first position and the device 30 is primed ready to commence an injection/medicament administration step.

As with the device 10 of the first embodiment, the device 30 of the second embodiment includes an adhesive patch 19 on the lower side 30b of the device 30 and a cover sheet 20 which covers the adhesive patch 19 and the sterilizing pad 18 prior to use and is removed by a user before using the device 30.

In the retracted position of the needle 13, the needle 13 is positioned between the sliding plate 34 and the upper side of the device 30a and, in the first position of the sliding plate 34, the sliding plate 34 is positioned between the needle 13 and the lower side 30b of the device 30, thereby blocking the needle 13 from being moved into the engaged position.

In use of the device 30, a patient detaches the cover sheet 20 from the lower side 30b of the device 30 to expose the adhesive patch 19 and the sterilizing pad 18. The patient then adheres the device 30 to an appropriate part of their body to serve as an injection site of the relevant medicament. The adhesive patch 19 secures the device 30 to the patient during the subsequent medicament administration process.

Once adhered to the body, the patient then slides the knob 36 across the slot 37 to move the sterilizing pad 18 from the first position to the second position and in doing so, the sterilizing pad 18 sweeps across the area of the patient's skin directly beneath the needle 13—namely the intended injection site. This sweeping movement of the sterilizing pad 18 over the skin allows the alcohol or other sterilizing agent in the pad 18 to disinfect the injection site ready for the medicament delivery injection to take place. The movement of the sliding plate 34 to the second (operative) position also moves the sliding plate 34 out of alignment with the needle 13 so that the needle 13 is no longer blocked from the patient's skin by the sliding plate 34 and so the needle 13 is then able to move from the retracted position to the engaged position.

In a subsequent medicament delivery step, the medicament delivery mechanism 12 is actuated to move the needle into the engaged position to pierce the patient's skin, and the medicament is then administered to the patient via the needle 13. The actuation of the medicament delivery mechanism may be manually initiated by the user, for example by pressing a button (not shown), or may occur automatically once the sliding plate 34 is moved into the second position.

As with the device 10 of the first embodiment, it will be appreciated that the device 30 of the second embodiment provides the advantages described above of eliminating the need for a user to perform a separate skin sterilizing step and reducing the number of pieces of equipment and materials the user needs to assemble in preparation for their medicament administration process. Also, the device 30 of the second embodiment provides a similar safety feature that the sliding plate 34 prevents the needle 13 from moving into the engaged position before the skin has been sterilized. The device 30 may include a further mechanism to prevent accidental actuation of the medicament delivery mechanism 12 before the sliding plate 34 has been moved into the second position. For example, a projecting element (not shown) on the web 35 may lock an actuator button until the web 35 is slid sufficiently across the slot 37 for the sliding plate 34 to be in the second position. Alternatively, the medicament delivery mechanism 12 may be actuated automatically only when the sliding plate 34 reaches the second position in the same way as described previously for the first embodiment.

The sterilizing pad 18 may be received within a recess 41 formed in the sliding plate 34 so as to be at least partially embedded within the sliding plate 34. This would provide the advantage of giving lateral support to the sterilizing pad 18 to counter the frictional resistance with the patient's skin as it sweeps across the patient's skin. The sterilizing pad 18 is preferably made from a compressible material and may initially be provided on the sliding plate 34 in a compressed state and which, upon detachment of the cover sheet 20, expands to stand proud of the surface of the sliding plate 34 and/or the lower side of the device 30. This ensures that the sterilizing pad 18 makes good contact with the patient's skin in use. In a further optional embodiment, the sterilizing pad 18 may be initially compressed within a recess 41 in the sliding plate 34 and retained in place by the cover sheet 20 being adhered to the surface of the sliding plate 34 around the recess 41 within which the sterilizing pad 18 is received. Then, upon detachment of the cover sheet 20, the sterilizing pad 18 may expand to project beyond the surface of the sliding plate 34.

It will be appreciated that the devices 10, 30 of the above-described embodiments are configured to sterilize a small area of the patient's skin immediately around the injection site. As such, the sterilizing agent which is impregnated into the sterilizing pad 18 may include a dye to color the area of the patient's skin that is sterilized during use of the device 10, 30. Once the device 10, 30 is removed after completion of the medicament administration process, the area of the injection site remains marked by the dye. This is advantageous as the patient can easily identify the area of their body last used as an injection site and ensure that the same site is not used again for the next successive medicament administration process. Furthermore, the configuration of the devices 10, 30 only sterilizing (and thereby dying) a small area immediately around the injection site means that the dyed area of skin is small and discrete, and so not unsightly. The dye used in the sterilizing agent may be configured to remain visible on the patient's skin for a pre-determined period of time, or predetermined number of washes of the skin, to correspond to the particular frequency of medicament administration. For example, if the medicament in question is intended for once weekly administration, the dye may be designed to stain the patient's skin for seven or eight days. This way, only the most immediately recent injection site would be visible to the patient and to avoid confusion as to which injection site was last used.

The sterilizing agent with which the sterilizing pad 18 is impregnated, or which is provided from the sterilizing mechanism, for example from the spray nozzle (see below), may optionally include a topical anesthetic to locally anesthetize the area of skin that is sterilized. This may beneficially reduce pain or discomfort that may otherwise be caused by injection of the needle into the patient's skin.

The sterilizing agent with which the sterilizing pad 18 is impregnated may be a liquid or a gel within the scope. An advantage of the sterilizing agent comprising a gel is that the agent would be less susceptible of leaking out from the sterilizing pad 18 during storage of the device 10, 30 and so the device 10, 30 may have a longer shelf or storage life.

Figure 10:
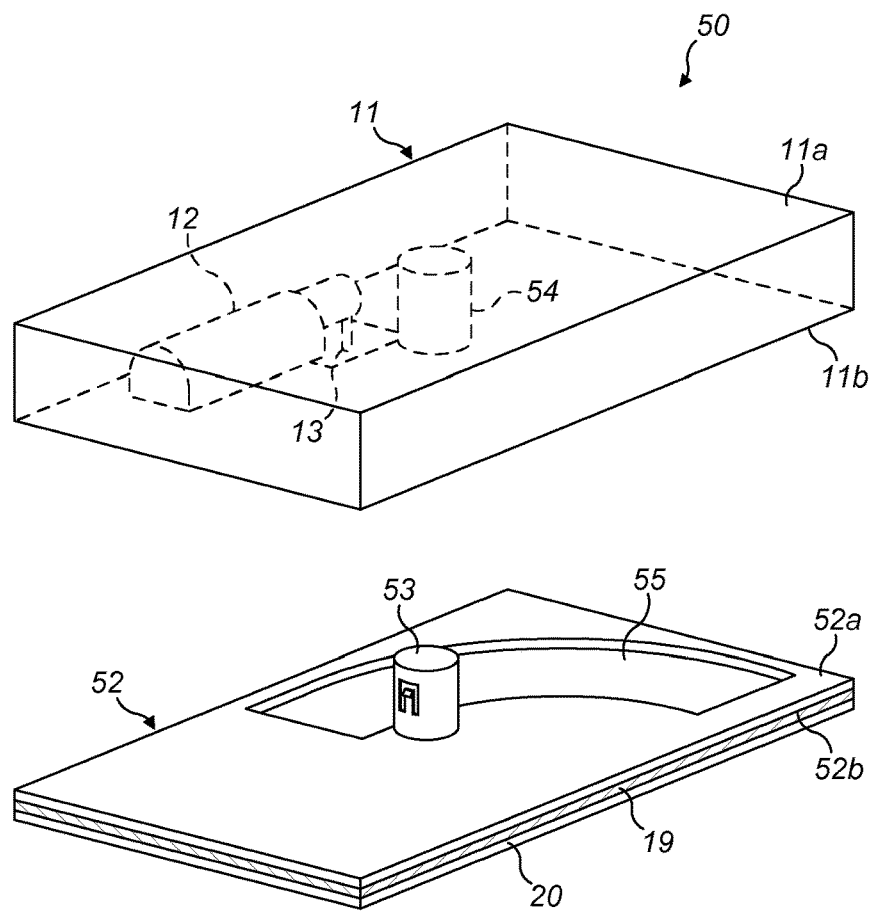
FIG. 10 shows an exploded perspective view of a medicament delivery device according to a third embodiment.
Figure 11:
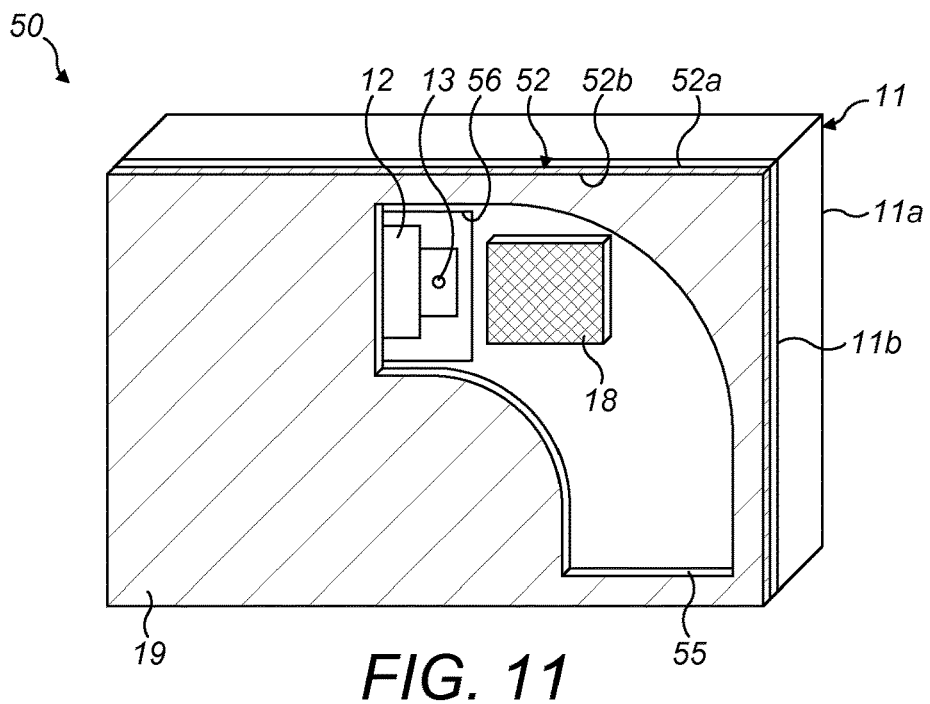
FIG. 11 shows a perspective view from below of the medicament delivery device of FIG. 10 in a first position and with a cover sheet removed.
Figure 12:
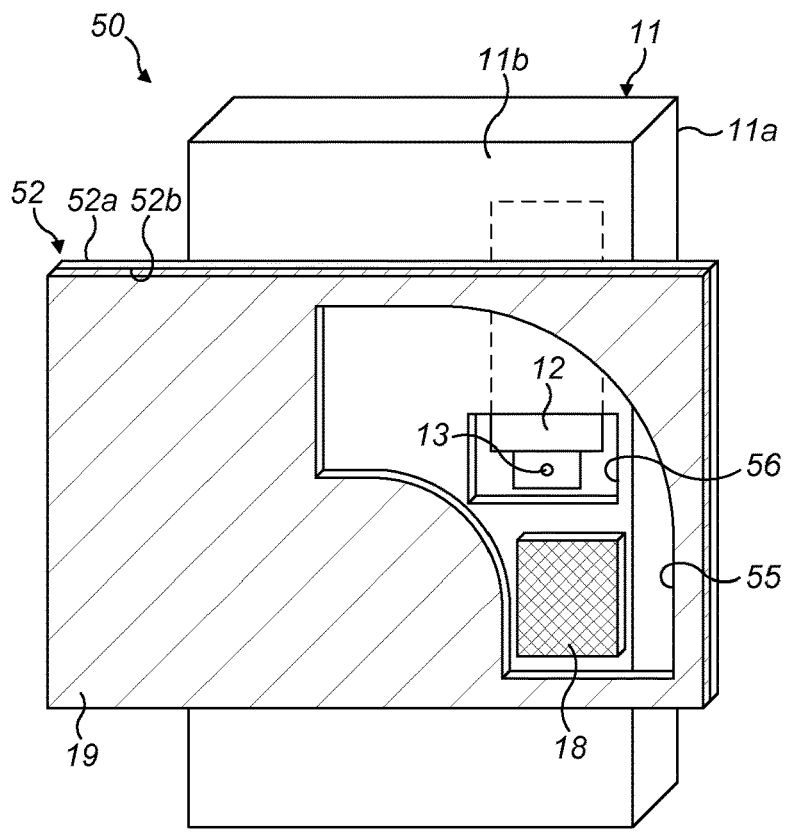
FIG. 12 shows a perspective view from below of the medicament delivery device of FIG. 10 in a second position and with a cover sheet removed.

The devices 10, 30 of the first and second embodiments comprise a sterilizing pad 18 that is mounted on a carrier which is moveably coupled to the housing 11 of the device. However, the invention is not intended to be limited to this particular configuration and it will be appreciated that the inventive concept includes providing a sterilizing pad incorporated into a medicament delivery device which can be wiped across an intended injection site on a patient's skin. As such, the sterilizing pad need not necessarily be movable relative to the housing 11 if, for example, the housing 11 is itself moveable once in place on a patient's skin. A device 50 of such an exemplary, third embodiment is shown in FIGS. 10 to 12. Like features with the first and second embodiments retain the same reference numerals. The device 50 generally comprises a housing 11 having an upper side 11*a* and a lower side 11*b*. The housing 11 is rotatably mounted to a base plate 52 by a post 53 upstanding from the base plate 52 being received in a cylindrical recess 54 in the lower side 11*b* of the housing 11. The base plate 52 has an upper side 52*a* and a lower side 52*b*. The adhesive patch 19 is provided on the lower side 52*b* of the base plate 52, and the cover sheet 20 is disposed over the adhesive patch 19.

The base plate 52 includes an arcuate aperture 55. The lower side 11*b* of the housing 11 includes a needle aperture 56. In the engaged position of the needle 13, the needle 13 extends out of the housing 11 through the needle aperture 56. The sterilizing pad 18 is fixed to the lower side 11*b* of the housing 11 adjacent the needle aperture 56. The housing 11 thereby serves as the sterilizing pad carrier. The housing 11 is movably mounted to the base plate 52 between a first position shown in FIG. 11 to a second position shown in FIG. 12. In the device 50 of the third embodiment, the housing 11 is rotatable relative to the base plate 52. In alternative embodiments, the housing 11 may be otherwise moveable relative to the base plate 52, for example by translation or sliding relative to the base plate 52. The sterilizing pad 18 projects from the lower side 11*b* of the housing and though the arcuate aperture 55. The sterilizing pad 18 may be compressible so that when the cover sheet 20 is in place, the sterilizing pad 18 is held at least flush with the lower side 52*b* of the base plate 52 in a compressed state. Upon removal of the cover sheet 20, the sterilizing pad 18 may expand to project through the arcuate aperture 55 beyond the lower surface 52b of the base plate 52. The cover sheet 20 may also serve to seal the sterilizing pad 18 prior to use of the device to avoid contamination of the sterilizing pad 18 and also to prevent the sterilizing pad 18 from drying out.

The device 50 is operated by moving the housing 11 from the first position to the second position. In the first position, the medicament delivery mechanism 12 is inoperable, but is operable once the housing 11 is moved into the second position. This may be achieved by a controller (not shown) connected to the medicament delivery mechanism 12 and a detector (not shown) connected to the controller to detect when the housing 11 is in the second position. Furthermore, the device 50 is shown in FIG. 11 with the needle aperture 56 being visible through the arcuate aperture 55 in the first position. However, the device 50 of the third embodiment may be alternatively configured such that the arcuate aperture 55 does not extend across the needle aperture 56 in the first position of the housing 11. Thereby, the needle would be blocked from moving into the engaged position by the base plate 52 while the housing is in the first position.

In use of the device 50 of the third embodiment, a patient detaches the cover sheet 20 exposing the adhesive patch 19 on the lower side 52b of the base plate 52 and secures the device 50 to their body using the adhesive patch 19. The sterilizing pad 18 expands and extends through the arcuate aperture 5 and into contact with the patient's skin. The patient then moves the housing 11 from the first position to the second position. The movement of the housing 11 causes the sterilizing pad 18 fixed to the housing to sweep across an intended injection site on a patient's skin. Once in the second position, the medicament administration process can commence. This may either be automatically actuated or by a patient-operated actuator such as a push button. The needle 13 then moves into the engaged position to pierce the patient's skin for medicament delivery at the sterilized injection site located within the outline of the arcuate aperture 55.

The sterilizing agent may comprise a dye for the reasons given previously.

It will be appreciated that the inventive concept of medicament delivery devices described herein may be applicable to LVDs. However, the invention is not intended to be limited to this particular type of medicament delivery device and the present invention is intended to cover alternative types of medicament delivery devices which function in contact with a patient's skin, such as, for example, patch pumps and infusion pumps.

The sterilizing pad 18 is described in the first and second embodiments as a material impregnated with a sterilizing agent. However, other configurations of sterilizing pad are intended to fall within the scope of the invention, for example a solid element of sterilizing material may be provided. Also, the invention is not limited to any particular shape of sterilizing pad 18, and the sector and rectangular sterilizing pad shapes shown in the first and second embodiments are exemplary only.

In the embodiments described above, the sterilizing pad is manually moveable across a patient's skin to sterilizing an intended injection site. However, the invention is not limited to such devices. Other embodiments may comprise alternative arrangements of actuator operable to move the sterilizing pad 18 across a patient's skin once the device is secured to the patient's body. For example, the sterilizing pad may be moved by an automated mechanism, for example, an electrically powered carrier plate may be mechanically coupled to an electric motor to be moved across an injection site. The device may include an actuator to independently control movement of the sterilizing pad to repeat a skin sterilizing step if needed or desired by a patient. For example, the actuator could allow multiple sweeps of the sterilizing pad across a patient's skin. For a device with manually moveable sterilizing pads, this is may be possible by a patient moving the actuator repeatedly. A controller may also control the medicament administration process. A patient may press a single button or other actuator to cause the sterilizing pad to be moved to sterilize the injection site. The medicament administration process may then automatically occur subsequent to the sterilization step. This may include automatic insertion of the injection and automatic delivery of the medicament to the patient.

The sterilizing pad 18 may comprise an absorbent pad impregnated with a suitable sterilizing agent. Exemplary sterilizing agents include, but are not limited to, isopropanol, isopropyl alcohol, isopropyl alcohol as a dissolution, for example isopropyl alcohol as a 70% dissolution, tincture of ionide, hydrogen peroxide, chloramine T, alcohol (e.g. ethanol, 1—propanol), phenols, nitrogen compounds, chlorhexidin, and/or detergents.

Devices intended to fall within the scope of the invention may include a hollow needle through which the medicament is delivered, or a solid needle, such as in trocar devices, in which a solid needle or obturator pierces the skin and a flexible hollow tube or cannula is subsequently inserted into the pierced hole and through which the medicament is subsequently delivered to the patient. In trocar devices, the solid needle or obturator does not remain in the patient's skin during medicament delivery.

The devices 10, 30, 50 of embodiments described above include an adhesive patch 19. However, devices may include other configurations of adhesive layer or adhesive surface, which may comprise a coating of adhesive applied directly to the housing 11 or base plate 52.

The devices 10, 30, 50 of embodiments described above include a sterilizing pad 18 that is moveable generally in a plane parallel to a patient's skin to sweep across the patient's skin in a sterilizing process. However, the invention is not intended to be limited to such a configuration and, in alternative embodiments, the sterilizing pad may be moveable relative to the adhesive surface to move towards and away from an injection site. In such an arrangement, the adhesive pad may move towards and into contact with the patient's skin in a "stamping" movement, and then move away from the skin to allow injection to occur in the sterilized injection site.

The devices 10, 30, 50 of embodiments described above include a sterilizing pad 18 that is moveable to contact a patient's skin in a sterilizing process. However, the invention is not intended to be limited to such a configuration, and devices of alternative embodiments may include an alternative arrangement of sterilizing mechanism that does not include a pad to contact the patient's skin. Such devices may, for example, include a sterilizing spray nozzle fluidly connected to a source of sterilizing agent. Upon attachment of the device to a patient's skin, the sterilizing means may be actuated to spray sterilizing agent onto an injection site before the needle injects the patient's skin. The sterilizing agent may be a fluid. The sterilizing agent may comprise a dye, for the reasons described previously. Yet further, the sterilizing mechanism may comprise a UV light generator to irradiate the injection site. Actuation of such sterilizing mechanisms may be manually operated or controlled electronically by a controller in a similar arrangement as described above.

Devices of embodiments may include means to prevent a sterilization step occurring before attachment of the device to a user's skin. This may be mechanical, such as a depressible button on the lower side 11b of the housing 11 or lower side 52b of the base plate 52 that is coupled to a locking mechanism connected to the sterilizing pad carrier. This may prevent movement of the carrier until the button is depressed—i.e. when the device is secured to a patient's body. Alternatively, the means may be electronic, such as a switch or sensor connected to a controller which control operation of the device and the sterilizing process. The controller may be prevented from operating the medicament administration process or the sterilization process until the sensor detects the device is secured to the patient's body.

The device is configured to deliver the medicament subcutaneously, although it may instead be configured for intradermal injection, for instance using a microneedle, or for injection in some other manner.

The bolus injector device may be of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device to simplify its operation by patients is highly desirable.

Because it is intended for bolus operation, the configuration of the injection device is quite different compared to an injection device that is intended to be used for basal operation. Also, its use is quite different. For instance, a basal type insulin pump generally is relatively expensive as it includes many sophisticated diabetes specific features like programmable delivery rate profiles, bolus calculators etc. Further, the connection to the body via an infusion set allows the patient to handle and manipulate the pump in his/her field of view while the therapy is ongoing. Further, diabetes patients usually have a routine in setting-up the infusion set, connecting and operating the pump, and disconnecting the pump temporarily for events like taking a shower so not to expose the pump to water. In contrast, the bolus injector devices described above can be relatively simple and inexpensive devices. They may be provided as single-use devices, which cannot be recharged with medicament, which further reduces complexity and cost.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra-low molecular weight heparin or a derivative thereof, or a sulphated, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient. Such an injection element may, for example, have an external size or diameter of 27 G or less. Further, the injection element could be rigid, flexible, and formed using a range of one or more materials. And in some embodiments, the injection element may include two or more components. For example, a rigid trocar may operate in conjunction with a flexible cannula. Initially, both the trocar and cannula may move together to pierce the skin. The trocar may then retract while the cannula remains at least partially within the target tissue. Later, the cannula may separately retract into the delivery device.

An insertion mechanism for inserting the needle may take any suitable form. It may be a mechanical spring based mechanism. Alternatively, the insertion element mechanism may for instance include an electric motor and a gear mechanism that causes insertion of the insertion element into the user. Alternatively, the insertion mechanism may be a gas or fluid pressure operated mechanism, in which case the needle driving energy source is either a reservoir of pressurized gas or a chemical system in which two or more chemicals are mixed together to produce gas or fluid pressure.

It will be appreciated that the embodiments shown in the figures are illustrated schematically for clarity and ease of illustration of the inventive concept, and the dimensions and proportions are not accurate. For example, the thicknesses of the adhesive layer 19 and cover sheet 20 are exaggerated.

The invention claimed is:

1. A medicament delivery device comprising a housing containing a medicament delivery mechanism including an injection needle, a sterilizing mechanism connected to the housing, and an adhesive surface for securing the device to skin of a patient during a medicament delivery process,
   wherein the sterilizing mechanism comprises a sterilizing pad impregnated with a sterilizing agent mounted on a carrier,
   wherein in use the sterilizing pad stands proud of a surface of a lower side of the device such that the pad is configured to contact the skin of the patient, and the sterilizing pad is repeatedly moveable relative to the adhesive surface such that in use when the device is secured to the skin of the patient, the sterilizing pad can be repeatedly moved into contact with the skin of the patient to sterilize an area of the skin of the patient to serve as an injection site, and
   wherein the injection needle is moveable between a retracted position in which the injection needle is fully disposed within the housing and an engaged position in which the injection needle projects from the housing to inject the skin of the patient in use,
   wherein the carrier is rotatably mounted to the housing,
   wherein the carrier is rotatable in a plane parallel to the skin of the patient between a first position and a second position, and
   wherein the injection needle is prevented from moving into the engaged position when the carrier is in the first position, and when the carrier is in the second position, the injection needle is free to move into the engaged position.

2. The medicament delivery device according to claim 1 wherein the sterilizing pad is received within a recess in the carrier.

3. The medicament delivery device according to claim 1 wherein the carrier comprises a rotatable plate.

4. A medicament delivery device according to claim 1 wherein when the carrier is in the first position, the carrier blocks a path of the injection needle to prevent it from being moveable into the engaged position.

5. The medicament delivery device according to claim 4 wherein the carrier comprises a circular plate with a sector absent, and wherein, in the second position of the carrier, the absent sector of the circular plate is aligned with the injection needle such that the injection needle can pass through the absent sector and into the engaged position.

6. The medicament delivery device according to claim 1 wherein the medicament delivery mechanism is coupled to the carrier such that the medicament delivery mechanism is prevented from operating when the carrier is in the first position and is operable when the carrier is in the second position.

7. The medicament delivery device according to claim 6 wherein the medicament delivery mechanism is actuated by a button on the housing and the button is prevented from actuating the medicament delivery mechanism when the carrier is in the first position.

8. The medicament delivery device according to claim 6 wherein the medicament delivery mechanism is electronically controlled and electrical power to actuate the medicament delivery mechanism is prevented when the carrier is in the first position.

9. The medicament delivery device according to claim 1 wherein the carrier is coupled to a control knob mounted on an outer surface of the housing and the carrier can be manually moved by moving the control knob.

10. The medicament delivery device according to claim 1 wherein the sterilizing agent comprises a dye to stain the skin of the patient.

11. The medicament delivery device according to claim 1 wherein the sterilizing agent comprises a gel.

12. The medicament delivery device according to claim 1 wherein the medicament delivery mechanism comprises a cartridge containing a drug.

13. A method of operating a medicament delivery device, the method comprising:
   securing a housing of the medicament delivery device to skin tissue of a patient by applying an adhesive surface of the medicament delivery device to the skin tissue;
   actuating a sterilizing mechanism disposed in the housing of the medicament delivery device to sterilize an area of the skin to serve as an injection site; and
   administering a medicament into the injection site,
   wherein the sterilizing mechanism comprises a sterilizing pad impregnated with a sterilizing agent mounted on a carrier, and actuating the sterilizing mechanism causes the sterilizing pad to stand proud of a surface of a lower side of the device such that the pad is in contact with the area of the skin,
   wherein the carrier is rotatably mounted to the housing, and
   wherein administering the medicament comprises moving an injection needle between a retracted position in which the injection needle is fully disposed within the housing and an engaged position in which the injection needle projects from the housing to inject the skin of a patient, and rotating the carrier in a plane parallel to the skin of the patient between a first position and a second position, and preventing the injection needle from moving into the engaged position when the carrier is in the first position, and freely moving the injection needle into the engaged position when the carrier is in the second position.

14. The method according to claim 13, wherein the sterilizing agent comprises a gel.

15. The method according to claim 13, wherein the sterilizing mechanism comprises a spray nozzle connected to a source of sterilizing agent and actuating the sterilizing mechanism causes the sterilizing agent to be sprayed onto a localized region of skin.

* * * * *